(12) United States Patent
Salciccioli et al.

(10) Patent No.: US 9,708,230 B2
(45) Date of Patent: Jul. 18, 2017

(54) PRODUCTION OF BIPHENYL COMPOUNDS

(71) Applicant: ExxonMobil Chemical Patents Inc.

(72) Inventors: Michael Salciccioli, Houston, TX (US); Jihad M. Dakka, Whitehouse Station, NJ (US); Neeraj Sangar, League City, TX (US); Lorenzo C. DeCaul, Langhorne, PA (US); Ali A. Kheir, Sugar Land, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/976,983

(22) Filed: Dec. 21, 2015

(65) Prior Publication Data

US 2016/0280616 A1 Sep. 29, 2016

Related U.S. Application Data

(60) Provisional application No. 62/137,996, filed on Mar. 25, 2015.

(51) Int. Cl.
*C07C 2/74* (2006.01)
*C07C 67/08* (2006.01)
(Continued)

(52) U.S. Cl.
CPC ............... *C07C 2/74* (2013.01); *C07C 5/367* (2013.01); *C07C 51/265* (2013.01); *C07C 67/08* (2013.01);
(Continued)

(58) Field of Classification Search
CPC ............ C07C 2521/08; C07C 2523/62; C07C 2529/74; C07C 2/74; C07C 5/367; C07C 67/08
(Continued)

(56) References Cited

U.S. PATENT DOCUMENTS 3,962,362 A * 6/1976 Suggitt ..................... C07C 2/74
585/252
6,037,513 A 3/2000 Chang et al.
(Continued)

OTHER PUBLICATIONS

U.S. Appl. No. 61/577,900, filed Dec. 20, 2011, Dakka et al.
(Continued)

*Primary Examiner* — Jafar Parsa
*Assistant Examiner* — Amy C Bonaparte

(57) ABSTRACT

In a process for producing biphenyl compounds, a $C_n$ aromatic hydrocarbon may be hydroalkylated to give $C_{2n}$ cycloalkylaromatic compounds and byproduct $C_n$ saturated cyclic hydrocarbons. The $C_{2n}$ cycloalkylaromatic compounds are dehydrogenated to provide the biphenyl compounds. The $C_n$ saturated cyclic hydrocarbons may also be dehydrogenated back to the corresponding $C_n$ aromatic hydrocarbon, which may be recycled to provide additional feed. Although both the intermediate $C_{2n}$ cycloalkylaromatic compounds and the byproduct $C_n$ saturated cyclic hydrocarbons should be dehydrogenated, at least part of the dehydrogenation of the $C_n$ saturated cyclic hydrocarbons should take place in the absence of $C_{2n}$ or greater hydrocarbons. Thus, dehydrogenation of the byproduct $C_n$ saturated cyclic hydrocarbons should take place at least in part separately from dehydrogenation of the $C_{2n}$ cycloalkylaromatic compounds.

22 Claims, 4 Drawing Sheets

(51) Int. Cl.
    *C07C 5/367* (2006.01)
    *C07C 51/265* (2006.01)
(52) U.S. Cl.
    CPC ...... *C07C 2521/08* (2013.01); *C07C 2523/42* (2013.01); *C07C 2529/74* (2013.01)
(58) Field of Classification Search
    USPC ......... 560/102; 562/412, 416, 417; 585/252, 585/25
    See application file for complete search history.

(56) References Cited

U.S. PATENT DOCUMENTS

| | | |
|---|---|---|
| 6,730,625 B1 | 5/2004 | Chang et al. |
| 2014/0275605 A1 | 9/2014 | Dakka et al. |
| 2014/0275606 A1 | 9/2014 | Bai et al. |
| 2014/0275607 A1 | 9/2014 | Dakka et al. |
| 2014/0275609 A1 | 9/2014 | Dakka et al. |
| 2014/0323782 A1 | 10/2014 | Chen et al. |

OTHER PUBLICATIONS

Godwin, "*Plasticizers*," Applied Polymer Science: 21st Century, 2000, pp. 157-175.
Sinfelt et al., "*Kinetics of Methylcyclohexane Dehydrogenation Over PT-Al$_2$O$_3$*," Journal of Physical Chemistry, vol. 64, 1960, pp. 1559-1562.
Sinfelt, "*The turnover frequency of methylcyclohexane dehydrogenation to toluene on a Pt reforming catalyst*," Journal of Molecular Catalysis A: Chemical, vol. 163, 2000, pp. 123-128.

\* cited by examiner

PRODUCTION OF BIPHENYL COMPOUNDS

PRIORITY

This invention claims priority to and the benefit of U.S. Ser. No. 62/137,996, filed Mar. 25, 2015.

FIELD OF THE INVENTION

The disclosure relates to methyl-substituted biphenyl compounds, their production and their use in the manufacture of plasticizers.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

The most important chemical class of plasticizers is phthalic acid esters, which accounted for about 84% worldwide of PVC plasticizer usage in 2009. However, there is an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. As a result, there is a need for non-phthalate, mono- or diester plasticizers, particularly oxo-ester plasticizers, that can be made from low cost feeds and employ few manufacturing steps in order to have comparable economics with their phthalate counterparts.

To this end, suggested substitutes for phthalates recently have included biphenylester-based plasticizers. For instance, U.S. Patent Publication No. 2014/0275609 teaches, among other things, the manufacture of dimethylbiphenyl compounds containing significant amounts of the 3,3'-dimethyl, the 3,4'-dimethyl and the 4,4'-dimethyl isomers. Such compounds can be economically produced by hydroalkylation of toluene and/or xylene followed by dehydrogenation of the resulting (methylcyclohexyl)toluene and/or (dimethylcyclohexyl)xylene product. As also taught in U.S. Patent Publication No. 2014/0275609, the resultant mixture can be used as a precursor in the production of biphenylester-based plasticizers by, for example, oxidizing the methyl-substituted biphenyl compounds to convert at least one of the methyl groups to a carboxylic acid group and then esterifying the carboxylic acid group with an alcohol, such as an oxo alcohol.

The proposed synthesis of dimethylbiphenyl compounds includes a first step of hydroalkylation of an aromatic hydrocarbon (e.g., benzene, toluene, and/or xylene, among others), which produces desired phenylcyclohexane and/or alkylated phenylcyclohexane intermediates, as well as undesired cyclohexane and/or alkylcyclohexane intermediate byproducts. These intermediates and intermediate byproducts can be dehydrogenated to form, respectively, (i) the desired biphenyl and/or dialkylbiphenyl product (e.g., dimethylbiphenyl) and (ii) benzene and/or alkylated benzene (e.g., toluene). Commercially desirable efficiency is achieved by separating and recycling the benzene and/or alkylated benzene for utilization as additional hydroalkylation feed.

The present inventors have found that the efficiency of the process can surprisingly be further improved by an additional, separate dehydrogenation of the cyclohexane and/or alkylcyclohexane intermediate byproducts in the absence of $C_{12}$ or greater hydrocarbons to provide benzene and/or alkylated benzene for the additional hydroalkylation feed.

Additional references of interest may include U.S. Pat. Nos. 6,730,625 and 6,037,513; U.S. Patent Publication Nos. 2014/0275605, 2014/0275606, 2014/0275607, 2014/0323782; Sinfelt, *J. Mol. Cat. A.*, 163 (2000), at 123; and Sinfelt et al., *J. Phys. Chem.*, 64 (1960), at 1559.

SUMMARY OF THE INVENTION

In one aspect, the present disclosure is directed to a process for producing biphenyl compounds. The process includes hydroalkylation of a feed comprising a $C_n$ aromatic hydrocarbon and hydrogen, where n may be from 6 to 12. The feed may include a mixture of $C_6$-$C_{12}$ aromatic hydrocarbons, in which case the "$C_n$ aromatic hydrocarbon" refers to the smallest (least number of carbon atoms) $C_6$-$C_{12}$ aromatic hydrocarbon in the feed. Suitable $C_6$-$C_{12}$ aromatic hydrocarbons include benzene, $C_7$-$C_{11}$ alkyl-substituted benzenes (such as toluene, xylene, ethylbenzene, and/or diethylbenzene), and $C_{10}$-$C_{12}$ naphthalenes (e.g., naphthalene and/or methyl, dimethyl, and/or ethyl-naphthalenes).

The hydroalkylation is carried out in the presence of a hydroalkylation catalyst under conditions effective to produce a hydroalkylation reaction effluent. The hydroalkylation comprises stepwise hydrogenation and alkylation, such that a portion of the $C_n$ aromatic hydrocarbons are partially hydrogenated to corresponding $C_n$ cyclic olefin intermediates, which in turn react in situ with a further portion of the $C_n$ aromatic hydrocarbons to form one or more $C_{2n}$ cycloalkylaromatic compounds. In addition, some of the $C_n$ aromatic hydrocarbons are completely hydrogenated (e.g., toluene may be completely dehydrogenated to methylcyclohexane). The hydroalkylation effluent therefore comprises (i) a $C_{2n}$ cycloalkylaromatic compound and (ii) a $C_n$ saturated cyclic hydrocarbon, in addition to any unreacted $C_n$ aromatic hydrocarbon feed. In certain aspects where n ranges from 6 to 12, the $C_{2n}$ cycloalkylaromatic compound is therefore a $C_{12}$-$C_{24}$ compound. For instance, where the $C_n$ aromatic hydrocarbon of the feed is toluene, the $C_{2n}$ cycloalkylaromatic compound is (methylcyclohexyl)toluene. Where $C_6$-$C_{12}$ aromatic hydrocarbons other than the $C_n$ aromatic hydrocarbons are present in the hydroalkylation feed, such $C_6$-$C_{12}$ aromatic hydrocarbons similarly undergo hydroalkylation to corresponding $C_{12}$-$C_{24}$ cycloalkylaromatic compounds.

Both the cycloalkylaromatic compounds and the saturated cyclic hydrocarbons are thereafter dehydrogenated. In particular, (i) the $C_{2n}$ cycloalkylaromatic compounds (and any other $C_{12}$-$C_{24}$ cycloalkylaromatic compounds) are dehydrogenated to one or more biphenyl compounds, the desired product; and (ii) the $C_n$ saturated cyclic hydrocarbons (and any other $C_6$-$C_{12}$ saturated cyclic hydrocarbons) are dehydrogenated to the corresponding aromatic hydrocarbons, which may advantageously be recycled to provide additional hydroalkylation feed.

Because both the cycloalkylaromatic compounds and the saturated cyclic hydrocarbons in the hydroalkylation effluent are dehydrogenated, it would conventionally be thought that both species should be dehydrogenated together in a single dehydrogenation zone, or in multiple dehydrogenation zones in series, without substantial separation of the cycloalkylaromatic compounds from the saturated cyclic hydrocarbons.

However, the present inventors have discovered that, counterintuitively, at least a portion of the saturated cyclic hydrocarbons should be dehydrogenated separately from the cycloalkylaromatic compounds.

Without wishing to be bound by theory, it is believed that the presence of higher hydrocarbons surprisingly reduces the conversion rate of the $C_n$ saturated cyclic hydrocarbon in the dehydrogenation reaction. Thus, a separation should be made so as to divide the smallest of the hydroalkylation product cycloalkylaromatic compounds from the saturated cyclic hydrocarbons. Thus, where a hydroalkylation feed comprises $C_6$-$C_{12}$ aromatic hydrocarbons, including a $C_n$ aromatic hydrocarbon which is the smallest (least number of carbon atoms) among the $C_6$-$C_{12}$ aromatic hydrocarbons, the separation should be made so as to provide (i) a light stream rich in the $C_n$ aromatic hydrocarbons, and (ii) a heavy stream rich in $C_{2n}$ (and heavier) cycloalkylaromatic compounds. That is, the dehydrogenation of saturated cyclic hydrocarbons should take place separately from any $C_{2n}$ or greater cycloalkylaromatic compound.

Therefore, the process according to some aspects further includes providing at least a portion of the hydroalkylation reaction effluent (comprising $C_n$ saturated cyclic hydrocarbons, and $C_{2n}$ cycloalkylaromatic compounds) to a first dehydrogenation zone, and therein dehydrogenating at least a portion of the $C_{2n}$ cycloalkylaromatic compound and at least a portion of the $C_n$ saturated cyclic hydrocarbon in the presence of a first dehydrogenation catalyst under conditions effective to produce a first dehydrogenation reaction product comprising (i) a mixture of $C_{2n}$ biphenyl compounds; (ii) a recovered $C_n$ aromatic hydrocarbon; and (iii) unreacted $C_n$ saturated cyclic hydrocarbon. At least a portion of the first dehydrogenation reaction product is thereafter separated into (i) a heavy dehydrogenation stream rich in the $C_{2n}$ biphenyl compounds, and (ii) a light dehydrogenation stream rich in the recovered $C_n$ aromatic hydrocarbon and the unreacted $C_n$ saturated cyclic hydrocarbon, and further depleted in the $C_{2n}$ biphenyl compounds. At least a portion of the light dehydrogenation stream is provided to a second dehydrogenation zone, wherein the unreacted $C_n$ saturated cyclic hydrocarbon in said portion of the light dehydrogenation stream is dehydrogenated to obtain additional recovered $C_n$ aromatic hydrocarbon. The recovered $C_n$ aromatic hydrocarbons may be recycled to provide additional hydroalkylation feed.

Alternatively, in other aspects, the process may include separation of the hydroalkylation reaction effluent, e.g., prior to any dehydrogenation. In such aspects, the process includes separating the hydroalkylation reaction effluent into (i) a heavy hydroalkylation effluent rich in the $C_{2n}$ cycloalkylaromatic compound, and (ii) a light hydroalkylation effluent rich in the $C_n$ saturated cyclic hydrocarbon, and depleted in the $C_{2n}$ cycloalkylaromatic compound. The process further includes providing at least a portion of the heavy hydroalkylation effluent to a first dehydrogenation zone, and therein dehydrogenating at least a portion of the $C_{2n}$ cycloalkylaromatic compound in the presence of a first dehydrogenation catalyst under conditions effective to produce a heavy dehydrogenation reaction product comprising a mixture of $C_{2n}$ biphenyl compounds. The light hydroalkylation effluent is provided to a second dehydrogenation zone, and therein at least a portion of the $C_n$ saturated cyclic hydrocarbon is dehydrogenated in the presence of a second dehydrogenation catalyst under conditions effective to produce a light dehydrogenation reaction product comprising a recovered $C_n$ aromatic hydrocarbon. The recovered $C_n$ aromatic hydrocarbon may be recycled to provide additional hydroalkylation feed.

DETAILED DESCRIPTION OF THE EMBODIMENTS

Figure 1:
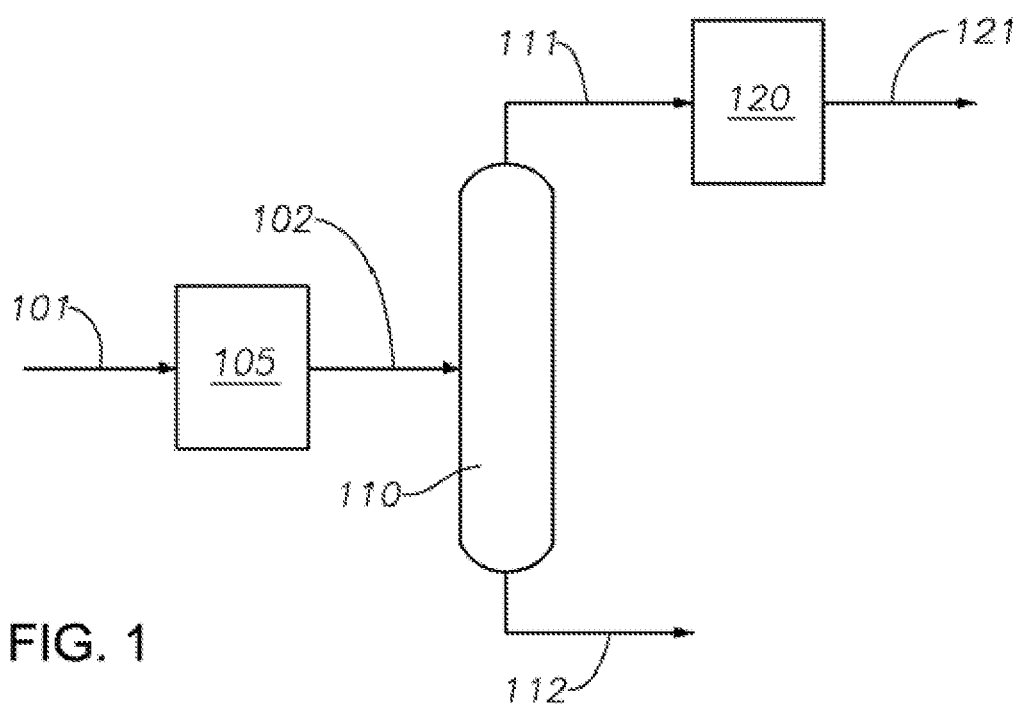
FIG. 1 is a simplified process flow diagram illustrating a biphenyl compound production process in accordance with some aspects of the present invention.

The present disclosure relates to the production of biphenyl compounds by the catalytic hydroalkylation of $C_n$ aromatic hydrocarbons such as $C_6$-$C_{12}$ aromatic hydrocarbons (e.g., benzene, toluene, xylene, ethylbenzene, diethylbenzene, and the like). Depending on the catalyst employed in the hydroalkylation reaction, the hydroalkylation process is selective to the production of the desired $C_{2n}$ cycloalkylaromatic compounds, which, depending on the aromatic hydrocarbon fed to the hydroalkylation process, may include any one or more of various $C_{12}$-$C_{24}$ cycloalkylaromatic compounds (e.g., phenylcyclohexane (also known as cyclohexylbenzene), (methylcyclohexyl)toluene, (dimethylcyclohexyl)xylene, (ethylcyclohexyl) ethylbenzene, and (diethylcyclohexyl) diethylbenzene. Nonetheless, fully saturated rings will also be produced as byproducts, such as $C_n$ (e.g., $C_6$-$C_{12}$ saturated cyclic hydrocarbons such as cyclohexane, methylcyclohexane, dimethylcyclohexane, ethylcyclohexane, and/or diethylcyclohexane, also depending upon the aromatic hydrocarbons present in the feed). The desired $C_{2n}$ cycloalkylaromatic compounds are dehydrogenated to form a mixture of biphenyl compounds, such as biphenyl, and/or methyl-, ethyl- or other alkyl-substituted biphenyl compounds. According to some embodiments, the mixture of biphenyl compounds includes dimethylbiphenyls (e.g., where the $C_7$ aromatic hydrocarbon toluene is present in the hydroalkylation feed). Such dimethylbiphenyl product of the dehydrogenation reaction contains significant amounts of the 3,3'-dimethyl, the 3,4'-dimethyl and the 4,4'-dimethyl compounds, making the product according to such embodiments an attractive precursor in the production of biphenylester-based plasticizers.

The byproduct $C_n$ saturated cyclic hydrocarbons are advantageously also dehydrogenated to recover $C_n$ aromatic hydrocarbons, which may be recycled to provide additional hydroalkylation feed. It is possible (and conventionally would be considered desirable) to conduct this additional dehydrogenation together with the dehydrogenation of the $C_{2n}$ cycloalkylaromatic compounds. However, the present inventors have discovered that substantial improvements in the conversion rate of $C_n$ saturated cyclic hydrocarbons to $C_n$ aromatic hydrocarbons are realized with dehydrogenation of the $C_n$ saturated cyclic hydrocarbons separately from $C_{2n}$ or greater cycloalkylaromatic compounds resulting from hydroalkylation of the $C_n$ aromatic hydrocarbon feed.

Definitions

As used herein, the numbering scheme for the Periodic Table Groups is as disclosed in Chemical and Engineering News, 63(5), 27 (1985).

As used herein, a "$C_x$ hydrocarbon," where x is an integer, refers to a hydrocarbon compound having X carbon atoms. Thus, a $C_6$ hydrocarbon is a hydrocarbon having 6 carbon atoms. A "$C_x$-$C_y$ hydrocarbon" is a hydrocarbon having from x to y carbon atoms (e.g., a $C_6$-$C_{10}$ hydrocarbon is a hydrocarbon having 6, 7, 8, 9, or 10 carbon atoms); a "$C_x$ or greater" hydrocarbon is a hydrocarbon having x or more carbon atoms; and a "greater than $C_x$ hydrocarbon" is a hydrocarbon having more than x carbon atoms. Similarly, a "$C_x$ or less" hydrocarbon is one having x or fewer carbon atoms, and "a less than $C_x$" hydrocarbon is one having fewer than x carbon atoms.

At certain points herein, reference is made to various "$C_n$" compounds. In such instances, unless otherwise indicated, n may be an integer ranging from 6 to 12, inclusive. Along these lines, a "$C_{2n}$" hydrocarbon is therefore a hydrocarbon having 2*n carbon atoms, with reference to a $C_n$ hydrocarbon, and a "$C_{3n}$" hydrocarbon is similarly a hydrocarbon having 3*n carbon atoms. For instance, where a $C_n$ hydrocarbon is given as a $C_7$ hydrocarbon (e.g., toluene), a $C_{2n}$ hydrocarbon would be a $C_{14}$ hydrocarbon. Where a mixture of multiple species of $C_6$-$C_{12}$ hydrocarbons is referred to, the $C_n$ hydrocarbon will be the smallest (least number of carbon atoms) among those $C_6$-$C_{12}$ hydrocarbons (thus, the mixture may be referred to as being of, e.g., $C_n$-$C_{12}$ hydrocarbons). Similarly, where a mixture of $C_{12}$-$C_{24}$ hydrocarbons is referred to, the $C_{20}$ hydrocarbon will be the smallest (least number of carbon atoms) among those $C_{12}$-$C_{24}$ hydrocarbons. Relatedly, then, a $C_{n+1}$ hydrocarbon may refer to a hydrocarbon having 1 more carbon atom than the $C_n$ hydrocarbon (such that a $C_n$-$C_{12}$ mixture may comprise a $C_n$ hydrocarbon and one or more $C_{n+1}$-$C_{12}$ hydrocarbons).

An "aromatic hydrocarbon" is a hydrocarbon containing an aromatic ring compound, and includes alkyl-substituted aromatic ring compounds. For instance, a $C_6$ aromatic hydrocarbon is an aromatic ring-containing hydrocarbon having 6 carbon atoms, such as benzene. Similarly, a $C_7$ aromatic hydrocarbon refers to a hydrocarbon compound containing an aromatic ring and having 7 carbon atoms, such as toluene. Thus, a "$C_6$-$C_{12}$ aromatic hydrocarbon," for example, is a hydrocarbon having 6-12 carbon atoms and containing an aromatic ring. Such hydrocarbons include, but are not necessarily limited to: benzene, toluene, ethylbenzene, xylene, diethylbenzene, propylbenzene, methylpropylbenzene, butylbenzene, and alkyl naphthalenes.

Along similar lines, a "saturated cyclic hydrocarbon" is a saturated hydrocarbon containing a carbon ring moiety. Thus, cyclohexane is an example of a $C_6$ saturated cyclic hydrocarbon. Similarly, methylcyclohexane is an example of a $C_7$ saturated cyclic hydrocarbon, and (dimethyl)cyclohexane and ethylcyclohexane are both examples of $C_8$ saturated cyclic hydrocarbons.

Similarly, a "$C_{12}$-$C_{20}$ cycloalkylaromatic compound" may refer to any of phenylcyclohexane (a $C_{12}$ hydrocarbon, also known as cyclohexylbenzene) and $C_{13}$-$C_{24}$ substituted phenylcyclohexanes containing a substituted moiety in place of one or more hydrogens on either the phenyl or cyclohexane moiety. Particularly contemplated $C_{13}$-$C_{24}$ substituted phenylcyclohexanes include alkyl-substituted phenylcyclohexanes (i.e., those containing one or more alkyl groups substituted in place of one or more hydrogens, such as (methylcyclohexyl)toluene, (dimethylcyclohexyl)xylene, or the like). As used herein, "alkyl-substituted" means one or more hydrogen atoms in the hydrocarbon is replaced by an alkyl moiety, such as methyl, ethyl, propyl, butyl, etc. In particular embodiments, the alkyl substitution may have from 1 to 10 carbon atoms, and in certain embodiments, from 1 to 5 carbon atoms. Also contemplated are $C_{16}$-$C_{24}$ cycloalkylaromatic compounds comprising a naphthyl and/or decalin moiety, such as cyclohexylnapthlalene (a $C_{16}$ substituted cycloalkylaromatic compound comprising a naphthyl moiety), and/or naphthyldecalin (a $C_{20}$ cycloalkylaromatic compound including both a naphthyl and decalin moiety). Either or both rings of such fused-ring structures may further contain an alkyl substitution.

As used herein, "biphenyl compounds" refer to biphenyl and/or substituted biphenyls. Thus, a $C_{12}$-$C_{24}$ biphenyl compound is a biphenyl or substituted biphenyl compound having 12-24 carbon atoms. Particularly contemplated are alkyl-substituted biphenyls, examples of which include biphenyl, dimethylbiphenyl, diethylbiphenyl, tetramethylbiphenyl, tetraethylbiphenyl, and so forth. Further, as with the cycloalkylaromatic compounds discussed above, also contemplated within this definition are biphenyl compounds in which either or both phenyl ring is substituted with a fused phenyl ring, such as in the case of a binaphthyl or alkyl-substituted binaphthyl compound.

Hydroalkylation of $C_n$ Aromatic Hydrocarbons

Hydroalkylation is a two-stage catalytic reaction in which an aromatic compound is partially hydrogenated to produce a cyclic olefin intermediate, which then reacts, in situ, with the aromatic compound to produce a cycloalkylaromatic product. In the present process, the aromatic compound comprises a $C_n$ aromatic hydrocarbon (preferably a $C_6$-$C_{12}$ aromatic hydrocarbon), and the cycloalkylaromatic product comprises one or more $C_{2n}$ (preferably $C_{12}$-$C_{24}$) cycloalkylaromatic compounds.

In some embodiments, the $C_n$ aromatic hydrocarbon is a $C_6$-$C_{12}$ aromatic hydrocarbon, such as benzene, a $C_7$-$C_{11}$ alkyl benzene, or a $C_{10}$-$C_{12}$ naphthalene or alkyl-substituted naphthalene. In certain embodiments, the $C_7$-$C_{11}$ alkyl benzene is selected from the group consisting of toluene, ethylbenzene, xylene, and diethylbenzene, with toluene and/or xylene being particularly preferred in certain embodiments. In particular embodiments, the $C_n$ aromatic hydrocarbon in the hydroalkylation feed is toluene or xylene. In some embodiments, the hydroalkylation feed may comprise multiple species of aromatic hydrocarbons (e.g., a mixture of toluene and xylenes). In such cases, as noted previously, the "$C_n$ aromatic hydrocarbon" refers to the smallest (lowest number of carbons) aromatic hydrocarbon. Thus, in the example given where toluene and xylene are present in the feed, n=7 (corresponding to toluene). Accordingly, the hydroalkylation feed of some embodiments may comprise one or more $C_n$-$C_{12}$ aromatic hydrocarbons, where n ranges from 6 to 12, and is the smallest species of aromatic hydrocarbon in the hydroalkylation feed.

Furthermore, it will be appreciated that in some preferred embodiments, where the hydroalkylation feed comprises a $C_6$ aromatic hydrocarbon (e.g., benzene), it is preferable that the hydroalkylation feed not contain a $C_{12}$ aromatic hydrocarbon (e.g., an alkyl naphthalene, or the like). This is because such $C_{12}$ aromatic hydrocarbons may be difficult to separate, by conventional means (e.g., fractionation), from the $C_{12}$ cycloalkylaromatic compounds that will result from hydroalkylation of the $C_6$ aromatic hydrocarbon. Further, as discussed elsewhere herein, $C_n$ aromatic hydrocarbon will form byproduct $C_n$ saturated cyclic hydrocarbon byproducts during hydroalkylation, which should be dehydrogenated at least in part separately from any $C_{2n}$ compounds. Of course, where n=6, this means dehydrogenation separately from $C_{12}$ compounds. Therefore, any $C_{12}$ aromatic hydrocarbons converted to $C_{12}$ cyclic hydrocarbon byproduct along with the $C_6$ cyclic hydrocarbon byproducts would not be retained in the $C_6$ cut of the separation, for further dehydrogenation and recycling. Such $C_{12}$ byproducts would therefore be significantly more difficult to recover for recycling.

A $C_n$ aromatic hydrocarbon will hydroalkylate to a desired corresponding $C_{2n}$ species by the aforementioned stepwise hydrogenation and alkylation process, as shown in the overall reaction scheme illustrated below for the example of toluene ($C_7$ aromatic hydrocarbon) feed:

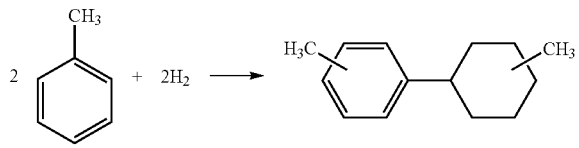

Thus, where a mixture of $C_n$-$C_{12}$ aromatic hydrocarbons is present in the hydroalkylation feed, a mixture of corresponding $C_{2n}$-$C_{24}$ cycloalkylaromatic compounds will be formed in the hydroalkylation reaction, where n ranges from 6-12.

Various reactions also compete with the hydroalkylation of the aromatic hydrocarbon. Among the competing reactions is further hydrogenation of the above-noted cyclic olefin intermediate and/or the cycloalkylaromatic product to produce fully saturated rings, such as one or more $C_6$-$C_{12}$ saturated cyclic hydrocarbons. Again returning to the example of toluene as the hydroalkylation feed, further hydrogenation can produce methylcyclohexane (a $C_7$ saturated cyclic hydrocarbon) and dimethylbicyclohexane compounds. Although these by-products can be converted back to feed (e.g., toluene) and to the product (e.g., (methylcyclohexyl)toluene and dimethylbiphenyl) via dehydrogenation, this involves an endothermic reaction requiring high temperatures (>375° C.) to obtain high conversion. This not only makes the reaction costly but can also lead to further by-product formation and hence yield loss. It is therefore desirable to employ a hydroalkylation catalyst that exhibits low selectivity towards the production of fully saturated rings.

Another competing reaction is dialkylation of the desired cycloalkylaromatic compound product. Again returning to the example of toluene hydroalkylation (in which (methylcyclohexyl)toluene is produced), the (methylcyclohexyl) toluene product reacts with further methylcyclohexene to produce di(methylcyclohexyl)toluene. Again this by-product can be converted back to (methylcyclohexyl)toluene, in this case by transalkylation. However, this process requires the use of an acid catalyst at temperatures above 160° C. and can lead to the production of additional by-products, such as di(methylcyclopentyl)toluenes, cyclohexylxylenes and cyclohexylbenzene. It is therefore desirable to employ a hydroalkylation catalyst that exhibits low selectivity towards di(methylcyclohexyl)toluene and other heavy by-products.

In addition to the aromatic hydrocarbon and hydrogen, a diluent, which is substantially inert under hydroalkylation conditions, may be included in the feed to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

The catalyst employed in the hydroalkylation reaction is a bifunctional catalyst comprising a hydrogenation component (e.g., a hydrogenation metal selected from group 10 of the Periodic Table of the Elements, with palladium being particularly advantageous) and a solid acid alkylation component, typically a molecular sieve. The catalyst may also include a binder such as clay, silica and/or metal oxides. In general, suitable hydroalkylation catalysts include those described in Paragraphs [0025]-[0029] of WIPO Publication No. 2014/159104 (published 2 Oct. 2014, with International Filing Date of 7 Mar. 2014), which is incorporated by reference herein.

A particularly preferred hydroalkylation catalyst, as noted therein, comprises a molecular sieve of the MCM-22 family. Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439, 409), SSZ-25 (described in U.S. Pat. No. 4,826,667), ERB-1 (described in EP 0 293 032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction effluent may comprise:

at least 60 wt %, such as at least 70 wt %, for example at least 80 wt % of the 3,3, 3,4, 4,3 and 4,4-isomers of (methylcyclohexyl)toluene based on the total weight of all the (methylcyclohexyl)toluene isomers;

less than 30 wt % of methylcyclohexane and less than 5 wt % of dimethylbicyclohexane compounds; and less than 3 wt % of compounds containing in excess of 14 carbon atoms.

Similarly, with a xylene feed, the hydroalkylation reaction effluent may comprise less than 3 wt % of compounds containing in excess of 16 carbon atoms. Likewise, with a diethylbenzene feed, the hydroalkylation reaction effluent may comprise less than 3 wt % of compounds containing in excess of 20 carbon atoms.

By way of illustration, the 3,3, 3,4 4,3 and 4,4-isomers of (methylcyclohexyl)toluene are illustrated in formulas F1 to F4, respectively:

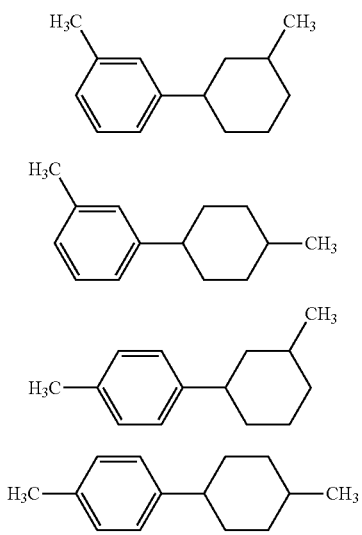

In contrast, when the methyl group is located in the 1-position (quaternary carbon) on the cyclohexyl ring, ring isomerization can occur forming (dimethylcyclopentyl)toluene and (ethylcyclopentyl)toluene which, on dehydrogenation, will generate diene by-products which are difficult to separate from the desired product and will also inhibit the subsequent oxidation reaction. In the oxidation and esterification steps, different isomers have different reactivity. Thus, para-isomers are more reactive than meta-isomers which are more reactive than ortho-isomers. Also in the dehydrogenation step, the presence of a methyl group in the 2 position on either the cyclohexyl or phenyl ring is a precursor for the formation of fluorene and methyl fluorene. Fluorene is difficult to separate from the dimethylbiphenyl product and causes problems in the oxidation step and also in the performance of plasticizers formed from the biphenyl compounds. It is therefore advantageous to minimize the formation of isomers which have a methyl group in the ortho, 2 and benzylic positions.

Dehydrogenation of Hydroalkylation Reaction Effluent

In processes according to some embodiments in which a hydroalkylation feed comprising a $C_n$ aromatic hydrocarbon is used, the major components of the hydroalkylation reaction effluent include: (i) unreacted $C_n$ aromatic hydrocarbons from the hydroalkylation feed (e.g., toluene or xylene); (ii) $C_n$ saturated cyclic hydrocarbon byproducts (e.g., methylcyclohexane or dimethylcyclohexane); (iii) the desired $C_{2n}$ cycloalkylaromatic product (e.g., (methylcyclohexyl)toluene or (dimethylcyclohexyl)xylene; and (iv) some dialkylated $C_{3n}$ or greater hydrocarbons. The identity of the dialkylated $C_{3n}$ or greater hydrocarbons will depend at least in part upon the aromatic hydrocarbon(s) present in the feed. Benzene (a $C_n$ aromatic hydrocarbon where n=6), for example, will lead to production of some $C_{18}$ (i.e., $C_{3n}$) dialkylated species (dicyclohexylbenzene), while toluene ($C_7$) will lead to production of some $C_{21}$ dialkylated species (di(methylcyclohexyl)toluene), etc. These species are labeled "dialkylated" because they have undergone the alkylation portion of the hydroalkylation reaction twice (e.g., a benzene, toluene, or the like has been alkylated with cyclic alkane twice).

As noted previously, it is also contemplated that the hydroalkylation feed may include mixtures of multiple species of $C_n$-$C_{12}$ aromatic hydrocarbons. In other words, the feed may further include, in addition to the $C_n$ aromatic hydrocarbons, one or more $C_{n+1}$-$C_{12}$ aromatic hydrocarbons. In such cases, the cycloalkylated products will further comprise $C_{2n+1}$-$C_{24}$ cycloalkylated compounds corresponding to the species in the feed. Likewise, the saturated cyclic hydrocarbon byproducts will further include $C_{n+1}$-$C_{12}$ saturated cyclic hydrocarbons corresponding to the aromatic species in the feed.

It is desired to dehydrogenate both the $C_{2n}$ cycloalkylaromatic compounds and the $C_n$ saturated cyclic hydrocarbon byproducts, such that the dehydrogenated cycloalkylaromatic compounds form the desired biphenyl compounds, and the dehydrogenated saturated cyclic hydrocarbons form additional aromatic hydrocarbon that may be recycled together with any unreacted aromatic hydrocarbons to provide additional hydroalkylation feed. Thus, the process may further comprise, after hydroalkylation, separating the dialkylated $C_{3n}$ or greater hydrocarbons from the hydroalkylation reaction effluent, leaving only the compounds to be dehydrogenated (cycloalkylaromatic compounds and saturated cyclic hydrocarbons) and the unreacted aromatic hydrocarbons to be recycled to the hydroalkylation reaction.

At this point, despite the desire to dehydrogenate both the cycloalkylaromatic compounds and saturated cyclic hydrocarbons, it is advantageous to perform at least one dehydrogenation of the $C_n$ saturated cyclic hydrocarbons separately from, or in the substantial absence of, $C_{2n}$ or greater hydrocarbons, including the $C_{2n}$ cycloalkylaromatic compounds. Thus, processes of certain embodiments include dehydrogenating at least a portion of the $C_n$ saturated cyclic hydrocarbons in the presence of less than about 5 wt %, more preferably less than about 1 wt %, even more preferably less than about 0.1 wt %, most preferably less than 0.01 wt %, of $C_{2n}$ or greater hydrocarbons, where n is an integer from 6 to 12. Particular embodiments include dehydrogenating at least a portion of the $C_n$ cyclic hydrocarbons in the presence of less than about 5 wt %, more preferably less than about 1 wt %, even more preferably less than about 0.1 wt %, most preferably less than about 0.01 wt %, of $C_{2n}$ or greater (such as $C_{2n}$-$C_{24}$) cycloalkylaromatic compounds and/or $C_{3n}$ or greater dialkylated hydrocarbons from the hydroalkylation reaction effluent. Conversion rate in the dehydrogenation of the saturated cyclic hydrocarbons is thereby substantially improved. Where one or more $C_{n+1}$-$C_{12}$ cyclic hydrocarbons also need to be dehydrogenated, preferably at least a portion of the $C_{n+1}$-$C_{12}$ cyclic hydrocarbons are also dehydrogenated in the presence of less than about 5 wt %, more preferably less than about 1 wt %, even more preferably less than about 0.1 wt %, most preferably less than about 0.01 wt %, of $C_{2n}$ or greater compounds. It will be appreciated that, where n=6, the portion of the $C_{n+1}$-$C_{12}$ cyclic hydrocarbons to be preferably dehydrogenated separately from the $C_{2n}$ or greater compounds will comprise only the $C_{n+1}$-$C_{11}$ cyclic hydrocarbons.

Accordingly, processes according to some embodiments include (i) dehydrogenation of at least a portion of the hydroalkylation effluent, which comprises both components ($C_n$ saturated cyclic hydrocarbons and $C_{2n}$ cycloalkylaromatic compounds); and (ii) subsequent dehydrogenation of at least a portion of the $C_n$ saturated cyclic hydrocarbons in the presence of less than about 5 wt % (more preferably less than about 1 wt %, even more preferably less than any one of about 0.1 wt % and 0.01 wt %) $C_{2n}$ or greater hydrocarbons (e.g., the cycloalkylaromatic compounds), where n is an integer from 6 to 12. In particular embodiments, n is 7 (e.g., for toluene feed) or 8 (e.g., for xylene feed). Such processes are illustrated in the simplified process flow diagram of FIG. 1.

Alternatively, processes according to other embodiments include: (i) first separating the $C_n$ saturated cyclic hydrocarbons from the $C_{2n}$ or greater hydrocarbons (including $C_{2n}$ cycloalkylaromatic compounds); and then (ii) dehydrogenating at least a portion of the $C_n$ saturated cyclic hydrocarbons in the presence of less than about 5 wt % (more preferably less than about 1 wt %, even more preferably less than any one of about 0.1 wt % and 0.01 wt %) $C_{2n}$ or greater hydrocarbons (including the cycloalkylaromatic compounds). The $C_{2n}$ cycloalkylaromatic compounds may also be dehydrogenated in an additional dehydrogenation reaction. Such processes are illustrated in the simplified process flow diagram of FIG. 2. As in embodiments in accordance with FIG. 1, n is an integer from 6 to 12 in embodiments in accordance with FIG. 2. In certain of these embodiments, n is 7 (e.g., for hydroalkylation feed including toluene as the smallest $C_6$-$C_{12}$ aromatic hydrocarbon) or 8 (e.g., for hydroalkylation feed including xylene as the smallest $C_6$-$C_{12}$ aromatic hydrocarbon).

Figure 2:
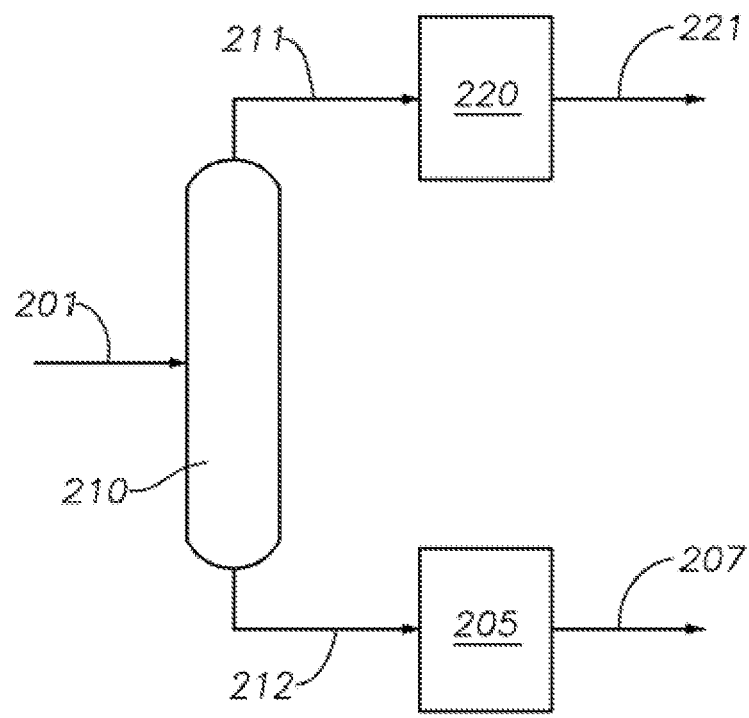
FIG. 2 is a simplified process flow diagram illustrating another biphenyl compound production process in accordance with some aspects of the present invention.

Each of the processes according to FIG. 1 and the processes according to FIG. 2 are discussed in greater detail below.

First, processes of some embodiments in accordance with FIG. 1 include: providing at least a portion of the hydroalkylation reaction effluent (shown in process stream 101) to a first dehydrogenation zone 105 to obtain a first dehydrogenation reaction effluent (shown in process stream 102). The desired reactions are: (i) dehydrogenation of the $C_{2n}$-$C_{24}$ cycloalkylaromatic compounds to corresponding biphenyl compounds, and (ii) dehydrogenation of $C_n$-$C_{12}$ saturated cyclic hydrocarbons to corresponding $C_n$-$C_{12}$ aromatic hydrocarbons (where n is an integer between 6 and 12, such as 7 or 8 in particular embodiments). However, because the dehydrogenation of the $C_n$ saturated cyclic hydrocarbons in the presence of $C_{2n}$ or greater hydrocarbons (e.g., the $C_{2n}$ cycloalkylaromatic compounds) will be incomplete, the first dehydrogenation reaction effluent in process stream 102 comprises (i) $C_{2n}$ biphenyl compounds; (ii) $C_n$ aromatic hydrocarbons; and (iii) unreacted $C_n$ saturated cyclic hydrocarbons. In some embodiments, the first dehydrogenation reaction effluent may further comprise (iv) unreacted $C_{2n}$ cycloalkylaromatic compounds.

The $C_{2n}$ and greater compounds (including the $C_{2n}$ biphenyl compounds, and any unreacted $C_{2n}$ cycloalkylaromatic compounds) are separated from the first dehydrogenation reaction effluent, e.g., via fractionation. In particular, the first dehydrogenation reaction effluent is separated into a heavy dehydrogenation effluent rich in the $C_{2n}$ compounds (including, but not necessarily limited to, the $C_{2n}$ biphenyl compounds and any unreacted $C_{2n}$ cycloalkylaromatic compounds) and a light dehydrogenation effluent rich in (a) the $C_n$ saturated cyclic hydrocarbon and (b) the $C_n$ aromatic hydrocarbon, where n is an integer from 6 to 12 (such as 7 or 8, in particular embodiments). The light dehydrogenation effluent may further comprise, where applicable, one or more $C_{n+1}$-$C_{12}$ saturated cyclic hydrocarbons and/or aromatic hydrocarbons (except where n=6, in which chase the light dehydrogenation effluent may further comprise one or more $C_{n+1}$-$C_{11}$ saturated cyclic hydrocarbons and/or aromatic hydrocarbons). Likewise, the heavy dehydrogenation effluent may comprise one or more $C_{2n+2}$-$C_{24}$ cycloalkylaromatic compounds. When an effluent, product, or other like mixture in a process stream is described herein as being "rich," "rich in," or "enriched" in one or more specified species, it is meant that the wt % of each specified species in that stream is enriched relative to the feed stream prior to separation. On the other hand, when a stream is described as being "depleted" in one or more specified species, it is meant that the wt % of each specified species in that stream is reduced relative to the feed stream prior to separation. Thus, a post-separation stream is "rich in $C_n$ saturated cyclic hydrocarbons and $C_n$ aromatic hydrocarbons" when the wt % of each of the $C_n$ saturated cyclic hydrocarbons and $C_n$ aromatic hydrocarbons in that stream is enriched (greater) relative to the wt % of each species in the corresponding stream prior to separation.

For example, FIG. 1 shows such separation in a distillation column 110, such that bottoms process stream 112 carries away the heavy dehydrogenation effluent, and top process stream 111 carries away the light dehydrogenation effluent.

The $C_{2n}$ biphenyl compounds of the heavy dehydrogenation effluent may be used in forming biphenyl ester plasticizers, as is described in greater detail below. Optionally, the heavy dehydrogenation effluent may be subjected to further separations and/or other treatment to obtain a product comprising at least 90 wt %, preferably at least 95%, more preferably at least 99 wt % biphenyl compounds. Optionally, at least a portion of the heavy dehydrogenation effluent may be recycled to the first dehydrogenation zone (e.g., to dehydrogenate unreacted cycloalkylaromatic compounds, if any, present in the heavy dehydrogenation effluent).

In particular embodiments, the light dehydrogenation effluent comprises less than about 5 wt %, preferably less than about 1 wt %, more preferably less than about 0.5 wt %, even more preferably less than about 0.1 wt %, and most preferably less than about 0.01 wt % of $C_{2n}$ or greater hydrocarbons (including, e.g., $C_{2n}$ cycloalkylaromatic compounds and/or $C_{2n}$ biphenyl compounds). That is to say, preferably, the separation of the first dehydrogenation effluent is carried out such that $C_{2n}$ and greater hydrocarbons are recovered in the bottoms fraction, and substantially not present in the light fraction. The exact conditions of the separation will depend at least in part upon the species present in the first dehydrogenation effluent. For instance, where the $C_n$ aromatic hydrocarbons fed to the initial hydroalkylation comprise toluene ($C_7$), it is expected that $C_{14}$ cycloalkylaromatic compounds (e.g., (methylcyclohexyl)toluene) and $C_{14}$ biphenyl compounds (e.g., dimethylbiphenyl) will be formed from hydroalkylation and dehydrogenation, respectively, while unreacted toluene and dehydrogenated unreacted toluene (i.e., methylcyclohexane, a $C_7$ saturated cyclic hydrocarbon) will also be present in the first dehydrogenation effluent. Such separation would therefore be run so as to remove a heavy dehydrogenation effluent of $C_{14}$ (and greater, as applicable) compounds, and a light dehydrogenation effluent of the $C_7$ compounds (which may further comprise any $C_8$-$C_{12}$ compounds, such as any unreacted $C_8$-$C_{12}$ aromatic hydrocarbons and/or saturated cyclic hydrocarbons, if present). An ordinarily skilled artisan will readily recognize suitable separation conditions, such as suitable distillation pressure and temperature, to separate the two sets of species $C_n$ and $C_{2n}$, given their amply different volatilities.

The light dehydrogenation effluent is subjected to a second dehydrogenation reaction in a second dehydrogenation zone 120 separate from the first dehydrogenation zone 105 to provide a second dehydrogenation effluent leaving in process stream 121. In the second dehydrogenation reaction, at least a portion of the $C_n$ saturated cyclic hydrocarbons are dehydrogenated to corresponding $C_n$ aromatic hydrocarbons (e.g., methylcyclohexane would be dehydrogenated to toluene). In some embodiments, at least about 90, preferably 95, more preferably 99, most preferably 99.9 wt % of the $C_n$ saturated cyclic hydrocarbons of the light dehydrogenation effluent are dehydrogenated in a single pass in the second dehydrogenation zone 120. In some embodiments, then, the resulting second dehydrogenation effluent (shown in process stream 121) may comprise less than 1 wt % (e.g., less than any one of 0.5 wt %, 0.1 wt %, and 0.01 wt %) $C_n$ saturated cyclic hydrocarbons. Further, in certain embodiments, the second dehydrogenation effluent comprises greater than about 80 wt %, preferably greater than about 90 wt %, more preferably greater than 95 wt %, most preferably greater than about 99 wt % $C_n$ aromatic hydrocarbons. The second dehydrogenation product may optionally be recycled to provide additional aromatic hydrocarbons to the hydroalkylation feed (not shown in FIG. 1).

Optionally, the second dehydrogenation product may be purified prior to being combined with the hydroalkylation feed. Any suitable separation technique may be used for such purification, such as fractionation, filtration, adsorption, absorption, and the like.

However, in some particularly advantageous embodiments, the dehydrogenation of $C_n$ saturated cyclic hydrocarbons separate from the $C_{2n}$ species, as provided herein, may facilitate conversions high enough so that distillation (or other like purification) after such separate dehydrogenation may not be necessary before recycling such dehydrogenation product back as hydroalkylation feed. For instance, in the case of MCH, the MCH concentration may be low enough coming out of such separate dehydrogenation such that MCH will not build up, interfere with, or substantially increase the recycle stream size for the hydroalkylation reactor. This can advantageously avoid the need to separate unreacted saturated cyclic hydrocarbons (e.g., MCH) from the recycled aromatic feed (e.g., toluene).

In further embodiments, purification (e.g., fractionation) of the second dehydrogenation product may still take place, but such purification may be operated at less severe conditions than would be required to separate a $C_n$ saturated cyclic hydrocarbon from its corresponding $C_n$ aromatic hydrocarbon (e.g., separating MCH from toluene, using the same example).

As noted, FIG. 2 provides a simplified illustration of processes according to other embodiments. In particular, such processes include separating the hydroalkylation reaction effluent (shown in process stream 201) into (i) a heavy hydroalkylation effluent rich in $C_{2n}$ and greater hydrocarbons (including the $C_{2n}$ cycloalkylaromatic compounds from the hydroalkylation reaction effluent), and (ii) a light hydroalkylation effluent rich in the $C_n$ saturated cyclic hydrocarbons from the hydroalkylation reaction effluent (where n is an integer from 6 to 12, such as 7 or 8, in particular embodiments). The light hydroalkylation effluent may, where applicable, further comprise one or more $C_{n+1}$-$C_{12}$ saturated cyclic hydrocarbons (or, where n=6, it may further comprise one or more $C_{n+1}$-$C_{11}$ saturated cyclic hydrocarbons). Similarly, the heavy hydroalkylation effluent may further comprise, where applicable, one or more $C_{2n+2}$-$C_{24}$ cycloalkylaromatic compounds.

The separation may be accomplished by any suitable means, such as fractionation. For example, in FIG. 2, the hydroalkylation effluent in process stream 201 is provided to a distillation column 210, with bottoms process stream 212 carrying away the heavy hydroalkylation effluent and top process stream 211 carrying away the light hydroalkylation effluent. In some embodiments, the light hydroalkylation effluent comprises less than about 5 wt %, preferably less than about 1 wt %, more preferably less than about 0.5 wt %, even more preferably less than about 0.1 wt %, and most preferably less than about 0.01 wt % of $C_{2n}$ or greater hydrocarbons (e.g., $C_{2n}$ cycloalkylaromatic compounds).

The process further comprises providing at least a portion of the heavy hydroalkylation effluent to a first dehydrogenation zone, and providing at least a portion of the light hydroalkylation effluent to a second dehydrogenation zone separate from the first. As shown in FIG. 2, the heavy hydroalkylation effluent is provided to a first dehydrogenation zone 205 via bottoms process stream 212, and the light hydroalkylation effluent is provided to a second dehydrogenation zone 220 via top process stream 211.

At least a portion of the heavy hydroalkylation reaction effluent is dehydrogenated in the first dehydrogenation reaction zone 205, providing a heavy dehydrogenation reaction product comprising a mixture of $C_{12}$-$C_{20}$ biphenyl compounds, shown in process stream 207 in FIG. 2. The biphenyl compounds may be useful in forming biphenyl ester plasticizers, as described below. The heavy dehydrogenation reaction product may further comprise unreacted $C_{2n}$ cycloalkylaromatic compounds. Accordingly, at least a portion of the heavy dehydrogenation reaction product may optionally be recycled to the first dehydrogenation zone to provide additional cycloalkylaromatic compound feed for the first dehydrogenation reaction (not shown in FIG. 2).

Similarly, at least a portion of the light hydroalkylation reaction effluent is dehydrogenated in the second dehydrogenation reaction zone 220, providing a light dehydrogenation reaction product comprising a recovered $C_n$ aromatic hydrocarbon (e.g., toluene and/or xylene), shown in process stream 221 in FIG. 2. The light dehydrogenation reaction product may further comprise a recovered $C_{n+1}$-$C_{12}$ recovered hydrocarbon (or, where n=6, a recovered $C_{n+1}$-$C_{11}$ recovered hydrocarbon). At least a portion of the recovered aromatic hydrocarbon(s) may be recycled to provide additional hydroalkylation feed (not shown in FIG. 2). In the dehydrogenation of the light hydroalkylation reaction effluent in the second dehydrogenation zone, at least about 90, preferably 95, more preferably 99, most preferably 99.9, wt % of the $C_n$ saturated cyclic hydrocarbons of the light hydroalkylation reaction effluent are dehydrogenated. Accordingly, the light dehydrogenation reaction product in process stream 221 may comprise less than 1 wt %, preferably less than 0.5 wt %, more preferably less than 0.1 wt % $C_n$ saturated cyclic hydrocarbons.

Further, in some embodiments, the light dehydrogenation reaction product may be further purified in any manner discussed above respecting the second dehydrogenation product of processes in accordance with FIG. 1. Alternatively, also as discussed with respect to processes in accordance with FIG. 1, it may advantageously not be necessary to provide for any purification of the light dehydrogenation reaction product; or, similarly, less severe purification conditions may be used. That is, as with processes in accordance with FIG. 1, any purification of the light dehydrogenation reaction product may be operated so as to remove higher or lower hydrocarbon species from the aromatic hydrocarbon that is desired to be recycled as hydroalkylation feed, but such purification need not be run at the (more severe) conditions necessary to separate a $C_n$ saturated cyclic hydrocarbon from its corresponding $C_n$ aromatic hydrocarbon.

In some embodiments according to any of the above-described processes (e.g., in accordance with either FIG. 1 or FIG. 2), as noted, the hydroalkylation reaction effluent comprises dialkylated $C_{3n}$ or greater hydrocarbons (where n, again, is an integer from 6 to 12). As also previously noted, such dialkylated $C_{3n}$ or greater hydrocarbons may be removed from the hydroalkylation reaction effluent prior to either or both dehydrogenation reactions. For example, in embodiments according to FIG. 1, $C_{3n}$ or greater hydrocarbons may be removed from the hydroalkylation effluent in process stream 101 via an additional distillation (or other suitable separation) step prior to the hydroalkylation effluent being provided to the first dehydrogenation zone 105. In embodiments according to FIG. 2, dialkylated $C_{3n}$ or greater hydrocarbons may be removed from the hydroalkylation effluent in a similar manner (e.g., additional distillation or other separation carried out on the hydroalkylation effluent in process stream 201) prior to the hydroalkylation reaction effluent being separated (e.g., at distillation column 210) into the light hydroalkylation effluent in stream 211 and the heavy hydroalkylation effluent in stream 212. Alternatively, the dialkylated $C_{3n}$ or greater hydrocarbons may be separated into the heavy hydroalkylation effluent in process stream 212 along with the $C_{2n}$ or greater hydrocarbons (e.g., the $C_{2n}$ cycloalkylaromatic compounds). An additional separation may therefore be employed in process stream 212 prior to the first dehydrogenation zone 205 to separate the dialkylated $C_{3n}$ or greater compounds from the $C_{2n}$ cycloalkylaromatic compounds in the heavy hydroalkylation effluent.

Each dehydrogenation zone in the processes of various embodiments (e.g., first and second dehydrogenation zones 105 and 120 in processes according to FIG. 1, and/or first and second dehydrogenation zones 205 and 220 in processes according to FIG. 2) may comprise one or more dehydrogenation reactors operating in series, in parallel, or in any combination thereof. Each dehydrogenation reaction is conducted at a temperature from about 200° C. to about 600° C. and a pressure from about 100 kPa to about 3550 kPa (atmospheric to about 500 psig) in the presence of dehydrogenation catalyst. In particular embodiments, dehydrogenation may be conducted at a temperature of from about 250° C. to about 500° C., preferably from about 300° C. to about 450° C., or from about 375° C. to about 450° C.

Hydrogen may be co-fed with the hydrocarbons to the dehydrogenation reaction (e.g., for catalyst stability purposes as described in co-pending U.S. Provisional Application No. 62/068,144). Where hydrogen is co-fed, the feed ratio (in terms of moles $H_2$ to moles hydrocarbons) may be within the range of about 0.5 to about 4.0, such as about 1.0 to about 3.0. Each dehydrogenation reactor may independently be any reactor suitable for dehydrogenation at such conditions (e.g., adiabatic fixed-beds in series, isothermal fixed-beds, etc.). Each dehydrogenation may be run at approximately the same conditions, or at different conditions. For instance, in some embodiments, dehydrogenation of the lighter cut (e.g., of the light hydroalkylation reaction effluent in embodiments in accordance with FIG. 2, or the light dehydrogenation effluent of embodiments in accordance with FIG. 1) may be run at a slightly higher temperature than dehydrogenation of a heavier cut.

The same or different dehydrogenation catalysts may be used in the dehydrogenation reactions described above. In general, suitable dehydrogenation catalysts include any dehydrogenation catalyst in accordance with those described in paragraphs [0055]-[0072] of US 2014/0275607, which is incorporated by reference herein. In some embodiments, as discussed therein, the dehydrogenation catalyst comprises one or more elements or compounds thereof selected from group 10 of the Periodic Table of Elements, for example platinum, on a refractory support. In one embodiment, the group 10 element is present in amount from 0.1 to 5 wt % of the catalyst. In some cases, the dehydrogenation catalyst may also include tin or a tin compound to improve the selectivity to the desired methyl-substituted biphenyl product. In one embodiment, the tin is present in amount from 0.05 to 2.5 wt % of the catalyst. In other embodiments, the tin may preferably be present in an amount from about 0.05 to about 0.30 wt %, more preferably from about 0.05 to about 0.15 wt %. The support employed in the dehydrogenation catalyst is refractory in the sense that it is capable of withstanding the conditions employed in the dehydrogenation reaction without physical or chemical changes. Non-limiting examples of suitable refractory support materials include: alumina, silica, silica-alumina, titania, calcium oxide, strontium oxide, barium oxide, magnesium oxide, carbon, zirconia, diatomaceous earth, lanthanide oxides including cerium oxide, lanthanum oxide, neodynium oxide, yttrium oxide and praesodynium oxide, oxides of chromium, thorium, uranium, niobium and tantalum, tin oxide, zinc oxide, and aluminum phosphate.

Further, as also discussed in US 2014/0275607, where the dehydrogenation catalyst contains tin, the catalyst may be prepared by impregnating the support with an aqueous solution of a suitable tin compound, such as tin chloride, and/or tin tartrate. The impregnated support containing Sn is then dried in air, such as at about 110° C. to about 130° C. (e.g., about 120° C.) for 4 hours, and then calcined, such as at about 350 to about 600° C. in air for 3 hours, to convert the tin to an oxide form. Afterwards, Pt is added to Sn-containing support by impregnation with an aqueous solution of a suitable platinum compound, such as $(NH_3)_4Pt(NO_3)_2$. The sample containing Sn and Pt is dried in air, such as at 120° C. for 4 hours, and then calcined, such as at a temperature between about 330° C. to about 370° C. (preferably about 350° C. to about 360° C.) in air for 3 hours.

In addition or instead, the dehydrogenation catalyst may be according to those described in Paragraphs [0020] to [0030] of US 2014/0323782, which is also incorporated by reference herein.

Processes utilizing multiple dehydrogenation zones according to some embodiments may use the same dehydrogenation catalyst in each of the multiple dehydrogenation zones. In some such embodiments where $C_n$ saturated cyclic hydrocarbons are dehydrogenated at least in part separately from $C_{2n}$ and greater hydrocarbons, less overall dehydrogenation catalyst may be used as compared to a process in which all dehydrogenation of $C_n$ saturated cyclic hydrocarbons takes place in the presence of $C_{2n}$ and greater hydrocarbons.

Production of Biphenyl Esters

Methyl-substituted biphenyl compounds (e.g., dimethylbiphenyl) produced by the processes of some embodiments can readily be converted to ester plasticizers by a process comprising oxidation to produce the corresponding carboxylic acids followed by esterification with an alcohol.

The oxidation can be performed by any process known in the art, such as by reacting the methyl-substituted biphenyl compounds with an oxidant, such as oxygen, ozone or air, or any other oxygen source, such as hydrogen peroxide, in the presence of a catalyst at temperatures from 30° C. to 300° C., such as from 60° C. to 200° C. Suitable catalysts comprise Co or Mn or a combination of both metals. Alternatively or in addition, the oxidation may take place in the presence of Br as an initiator.

The resulting carboxylic acids can then be esterified to produce biphenyl ester plasticizers by reaction with one or more $C_4$ to $C_{14}$ alcohols. Suitable esterification conditions are well-known in the art and include, but are not limited to, temperatures of 0-300° C. and the presence or absence of homogeneous or heterogeneous esterification catalysts, such as Lewis or Bronsted acid catalysts. Suitable alcohols include "oxo-alcohols," by which is meant an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. Another source of olefins used in the OXO process are through the oligomerization of ethylene, producing mixtures of predominately straight chain alcohols with lesser amounts of lightly branched alcohols.

The biphenyl ester plasticizers of the present application find use in a number of different polymers, such as vinyl chloride resins, polyesters, polyurethanes, ethylene-vinyl acetate copolymers, rubbers, poly(meth)acrylics and mixtures thereof.

The invention will now be more particularly described with reference to the following non-limiting Examples.

EXAMPLES

Example 1: General Procedure for Toluene Hydroalkylation

A palladium MCM-49 hydroalkylation catalyst was loaded into a hydroalkylation reactor. The reactor comprised a stainless steel tube having an outside diameter of: ⅜ inch (0.95 cm), a length of 20.5 inch (52 cm) and a wall thickness of 0.35 inch (0.9 cm). A piece of stainless steel tubing having a length of 8¾ inch (22 cm) and an outside diameter of: ⅜ inch (0.95 cm) and a similar length of ¼ inch (0.6 cm) tubing of were used in the bottom of the reactor (one inside of the other) as a spacer to position and support the catalyst in the isothermal zone of the furnace. A ¼ inch (0.6 cm) plug of glass wool was placed on top of the spacer to keep the catalyst in place. A ⅛ inch (0.3 cm) stainless steel thermowell was placed in the catalyst bed to monitor temperature throughout the catalyst bed using a movable thermocouple.

The catalyst was sized to 20/40 sieve mesh or cut to 1:1 length to diameter ratio, dispersed with quartz chips (20/40 mesh) then loaded into the reactor from the top to a volume of 5.5 cc. The catalyst bed typically was 15 cm. in length. The remaining void space at the top of the reactor was filled with quartz chips, with a ¼ plug of glass wool placed on top of the catalyst bed being used to separate quartz chips from the catalyst. The reactor was installed in a furnace with the catalyst bed in the middle of the furnace at a pre-marked isothermal zone. The reactor was then pressure and leak tested typically at 300 psig (2170 kPa).

The catalyst was pre-conditioned in situ by heating to 25° C. to 240° C. with $H_2$ flow at 100 cc/min and holding for 12 hours. A 500 cc ISCO syringe pump was used to introduce a chemical grade toluene feed to the reactor. Commercially available chemical grade Toluene and hydrogen feed (2:1 ratio moles $H_2$ to moles toluene) was pumped through a vaporizer before flowing through heated lines to the reactor. A Brooks mass flow controller was used to set the hydrogen flow rate. A Grove "Mity Mite" back pressure controller was used to control the reactor pressure typically at 150 psig (1135 kPa). GC analyses were taken to verify feed composition. The feed was then pumped through the catalyst bed held at the reaction temperature of 120° C. to 180° C. at a WHSV of 2 and a pressure of 150 psig (~1135.5 kPa). Non-condensable gas products were routed to an online HP 5890 GC. The liquid products exiting the reactor flowed through heated lines routed to two collection pots in series, the first pot being heated to 60° C. and the second pot cooled with chilled coolant to about 10° C. Material balances were taken at 12 to 24 hour intervals. A Hewlett Packard 6890 gas chromatograph with FID detector was used for analysis.

The liquid products of the hydroalkylation reaction were found to include about 25 wt % (methylcyclohexyl)toluene (MCHT); about 8 wt % methylcyclohexane (MCH); about 66 wt % unreacted feed; and about 1 wt % byproducts.

Example 2: Dehydrogenation of Hydroalkylation Reaction Effluent

Liquid hydroalkylation products were used as feed in a dehydrogenation reaction. The liquid hydrocarbon feed to dehydrogenation according to Example 2 comprised about 25 wt % (methylcyclohexyl)toluene (MCHT); about 8 wt % methylcyclohexane (MCH); about 66 wt % unreacted feed; and about 1 wt % byproducts. Three runs of the dehydrogenation reaction were carried out at different weight hourly space velocities (WHSVs)—in particular, WHSVs of 2, 4, and 8, corresponding to runs 2-1, 2-2, and 2-3, as shown in Table 1 (as shown in Table 1, WHSV was varied by varying the amount of catalyst loaded and maintaining the same feed rate).

TABLE 1

Dehydrogenations of Hydroalkylation Reaction Effluent

| Run | Amount of Catalyst (g) | WHSV | MCH Conversion | MCHT conversion |
|---|---|---|---|---|
| 2-1 | 1 | 2 | 80.5% | 83.5% |
| 2-2 | 0.5 | 4 | 60.8% | 81.5% |
| 2-3 | 0.25 | 8 | 46.9% | 76.5% |

The dehydrogenation was carried out at 430° C. and 100 psig in a dehydrogenation reaction system comprising 8 parallel reactors. An ISCO syringe pump was used to introduce the feed to the reactors. The liquid hydrocarbon feed was pumped through a vaporizer before being mixed in-line with $H_2$ at a 2:1 molar ratio of $H_2$ to liquid feed, then delivered to each reactor.

The 8 parallel reactors were placed in a fluidized heated sand bath to control isothermal reaction temperature. Each reactor was a U-shaped stainless steel reactor of 5 mm inner diameter. Half of the U-shaped downflow path (39 cm long) was used as a preheating zone filled with quartz chips (20/40 mesh). Dehydrogenation catalyst was loaded into the upflow portion of the back-end of the U-shaped reactor, with quartz wool plugs at the top and bottom of the catalyst bed to keep it in place. Catalyst quantities ranged from about 0.25-1 g, depending on WHSV (as shown in Table 1).

The dehydrogenation catalyst (1 wt % platinum and 0.15 wt % tin deposited on an $SiO_2$ support) was prepared as follows: a 1/20" quadrulobe silica extrudate was initially impregnated with an aqueous solution of tin chloride and then dried in air at 121° C. The resultant tin-containing extrudates were then impregnated with an aqueous solution of tetraamine Platinum nitrate and again dried in air at 121° C. Each of the resultant catalyst products was then calcined in air at 350° C. for 3 hours before being used in the dehydrogenation reaction.

Catalyst in all reactors was pre-conditioned in situ, starting with $N_2$ flow to dry the catalyst (at 50 cc/min total for all 8 reactor channels) at atmospheric pressure and 25° C. The temperature was then ramped to 80° C. at a rate of 25° C./hour and held for 3 hours. The temperature was then ramped to 120° C. at a rate of 25° C./hour and held at that temperature for an additional 3 hours. After the drying step, the catalysts in each reactor were reduced in $H_2$ at a total flow rate (combined for all reactors) of 111.2 sccm. The pressure was then increased to the reaction pressure of 100 psig and held for 20 min. The temperature was then ramped to 450° C. at a rate of 25° C./hour and held at this temperature for 2 hours. Finally, the temperature was reduced to the desired isothermal reaction temperature.

The products exiting the reactor system were condensed and collected in intervals (approximately one sample per day per reactor) and analyzed by GC in the same manner as indicated in Example 1.

Figure 3:
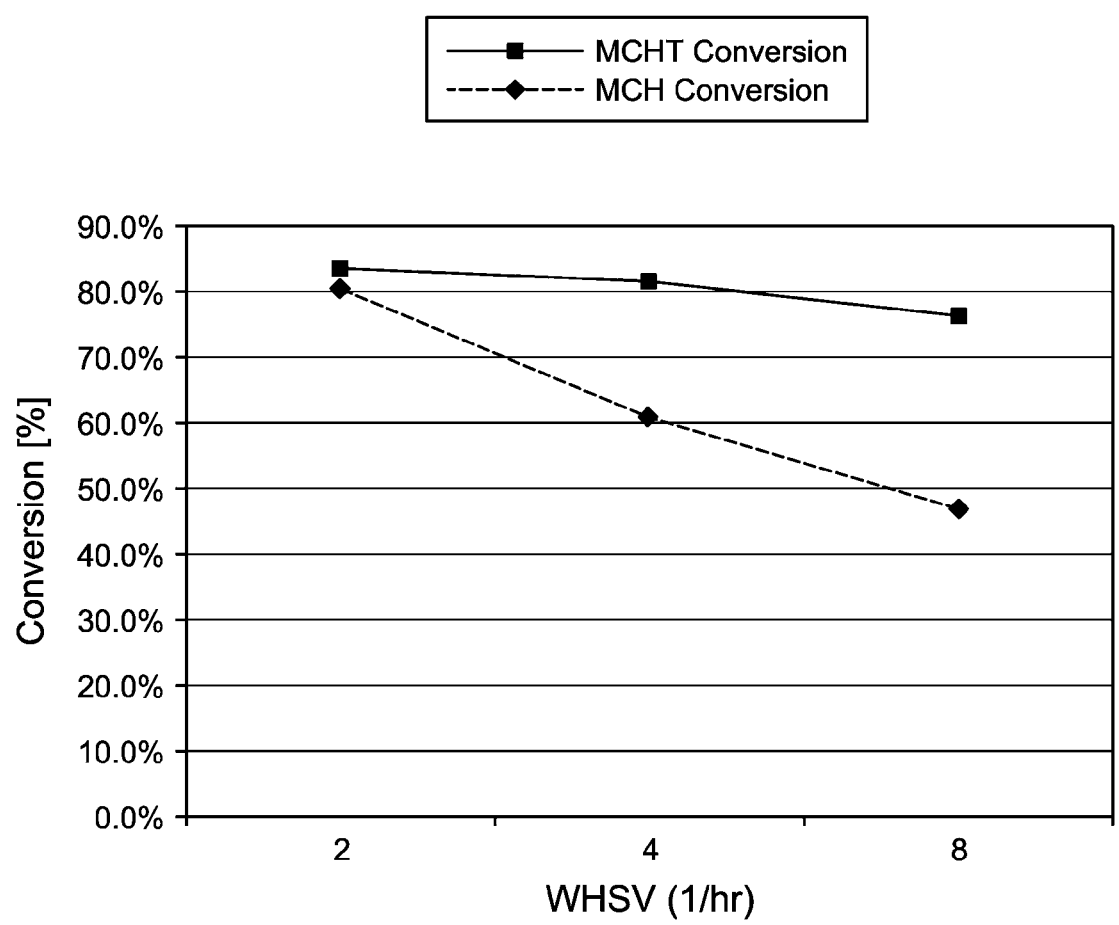
FIG. 3 is a graph of methylcyclohexane (MCH) and (methylcyclohexyl)toluene (MCHT) conversion against weight hourly space velocity (WHSV) in the dehydrogenation of MCH and MCHT according to Example 2.

Table 1 and FIG. 3 illustrate the conversion of each of MCHT (a $C_{14}$ cycloalkylaromatic compound) and MCH (a $C_7$ saturated cyclic hydrocarbon) in the dehydrogenation of Example 2. As seen in FIG. 3, conversion of MCH in the presence of MCHT is at best around 80% at lowest WHSV. Furthermore, with increasing WHSV, conversion of MCH drops off (more so than the decrease in MCHT conversion), from about 80% (at 2 WHSV) to less than 50% (at 8 WHSV), therefore indicating a substantial tradeoff between process throughput and efficiency when MCH is dehydrogenated in the presence of MCHT.

Example 3: Dehydrogenation After Separating $C_{21}$ and Greater Hydrocarbons

The hydroalkylation effluent from Example 1 was fractionated via batch distillation into (i) a heavy fraction comprising $C_{21}$ and heavier byproducts and (ii) a light fraction comprising 7 wt % MCH and 16.5 wt % MCHT, 75.7 wt % toluene, and about 0.8 wt % other hydroalkylation byproducts and impurities (including, but not limited to, cyclohexane, dimethylbicyclohexane, xylenes, and benzene).

The light fraction was provided to a dehydrogenation reactor system using the same varying feed rates (2, 4, and 8 WHSV) described in Example 2. Thus, the dehydrogenation of this example also involved dehydrogenation of both MCH and MCHT together; however, unlike the dehydrogenation of Example 2, $C_{21}$ and greater hydrocarbons were not present in substantial amounts. An ISCO syringe pump was used to introduce feed to the reactor system. The feed was pumped through a vaporizer before being mixed inline with $H_2$ at a 2:1 ratio (moles $H_2$ to moles liquid feed), then delivered to the reactor system. The dehydrogenation reactor system was similar to that described in Example 2, except that the 8 parallel reactors in these experiments were quartz tubes of 9 mm inner diameter, and heated by furnace instead of sand bath.

Figure 4A:
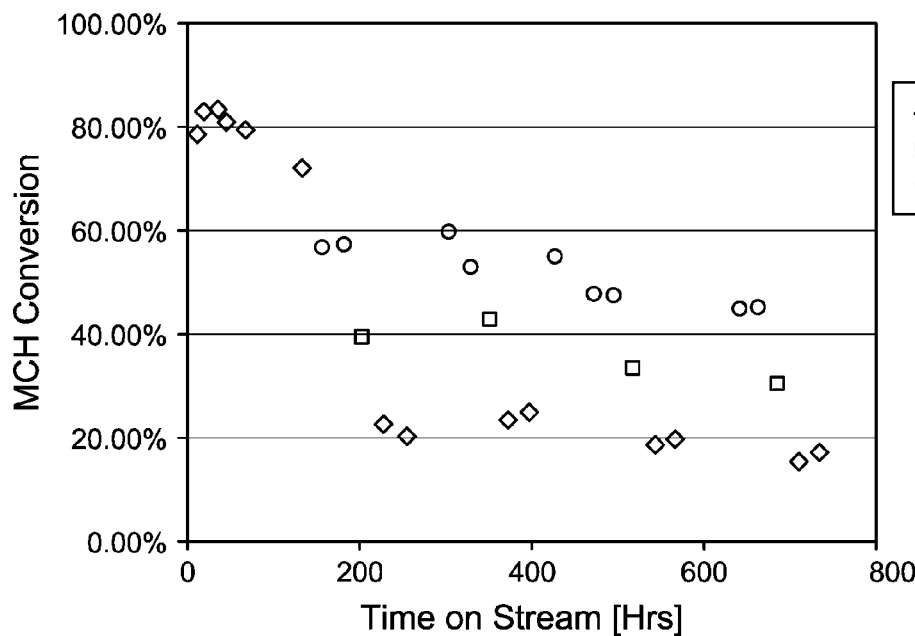
FIGS. 4a and 4b are graphs of MCH and MCHT conversion, respectively, against time on stream (TOS) in the dehydrogenation of MCH and MCHT according to Example 3.
Figure 4B:
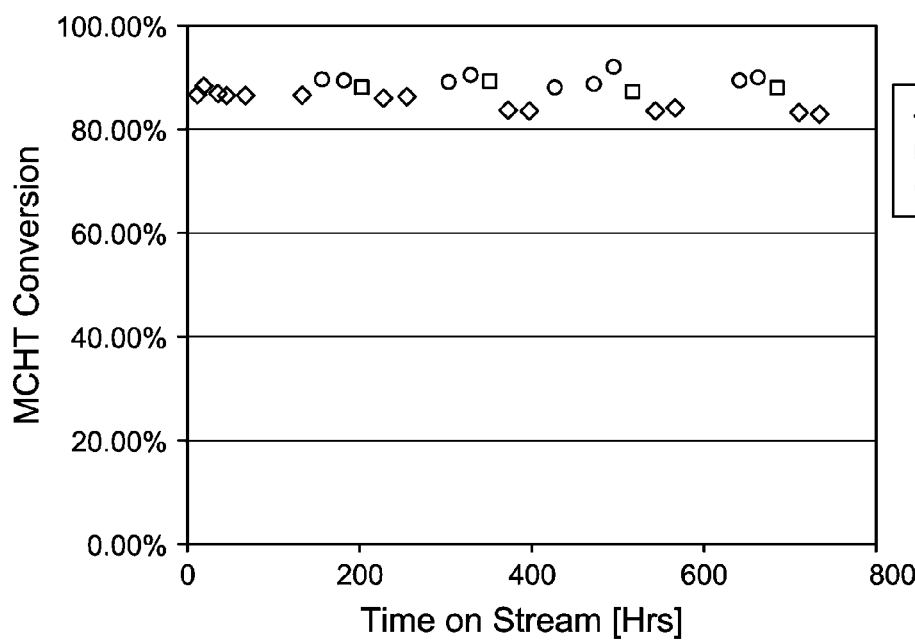

As shown in FIGS. 4a and 4b, even in the substantial absence of $C_{21}$ and greater hydrocarbons, the dehydrogenation of MCH suffers from the presence of MCHT, both at higher rates (WHSV), and at greater time on stream. As shown in FIG. 4a, at 8 WHSV, MCH conversion starts at around 80%, but drops off to 70% after just over 100 hours on stream, and then to approximately 20% after 200 hours on stream. Similarly, at 4 WHSV, MCH conversion quickly drops from 80% initially to about 40% after 200 hours on stream, and from there declines to 20% after 500 hours on stream. At 2 WHSV, MCH conversion declines more steadily, reaching 60% after 200 hours on stream, and just over 40% after 600 hours on stream. By contrast, as shown in FIG. 4b, MCHT conversion holds steady at over 80% at each of 2, 4, and 8 WHSV.

Example 4: Dehydrogenation of MCH in the Absence of $C_{12}$ or Greater Hydrocarbons Nearly pure MCH (>99.5% purity) was dehydrogenated over the same dehydrogenation catalyst packed in a 3/8 inch (0.95 cm) outer diameter×16.5 inch (41.91 cm) length stainless steel reactor. The catalyst bed was centered in the isothermal zone of the reactor, with quartz wool and additional quartz chips packed into the reactor to hold the catalyst bed in place. The reactor was first purged with hydrogen and pressurized to 100 psig, then heated at 5° C./minute to 425° C. with hydrogen flow through a first ISCO pump at 100 cc/min. Reactor temperature was maintained at 425° C. for about two hours, then MCH was fed to the reactor at 2 WHSV through a second 100 cc ISCO pump, and $H_2$ flow was reduced to 30 cc/min. Reaction temperature was maintained at 425° C., lower than the 450° C. of dehydrogenation with MCH and MCHT together, as thermodynamic calculations indicated that temperatures as low as 400° C. would theoretically provide 100% conversion.

Liquid product was collected in cold traps for analysis. Material balances were taken over 16 to 24 hours. A sample from each material balance was taken and analyzed on a HP 7890 GC with a Beta Dex-120 column. The Beta Dex-120 column dimensions were 60 m length×0.25 mm outer diameter×0.25 micron film thickness.

Figure 5:
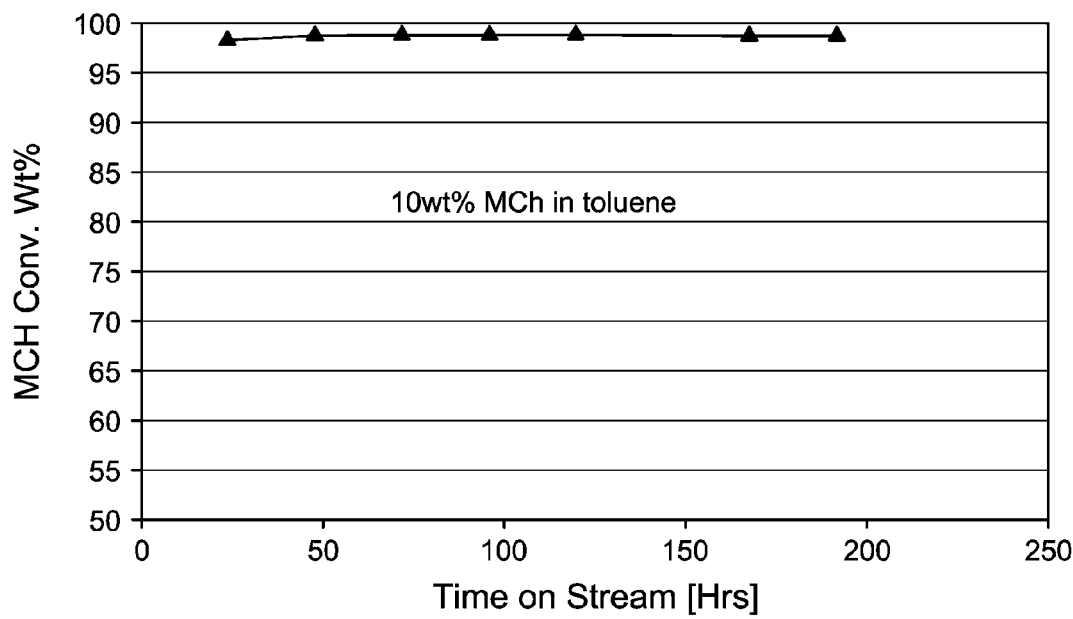
FIG. 5 is a graph of MCH conversion against time on stream (TOS) in the dehydrogenation of MCH according to Example 4.

As shown in FIG. 5, MCH conversion was maintained at nearly 100% for the entire time on stream (almost 200 hours), indicating significantly better conversion in the absence of heavier hydrocarbons such as the $C_{14}$ MCTH.

Example 5: Dehydrogenation of Feed Comprising MCH and Toluene

Figure 6:
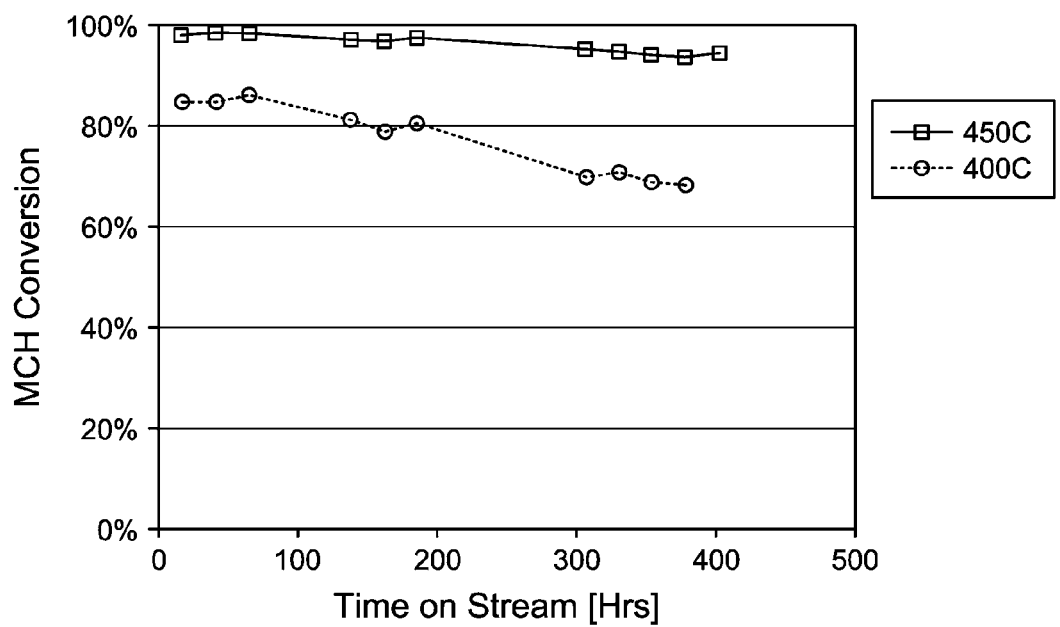
FIG. 6 is a graph of MCH conversion against time on stream in the dehydrogenation of MCH in the presence of toluene, according to Example 5.

Hydroalkylation effluent was dehydrogenated in the dehydrogenation reactor described in Example 3. The dehydrogenation product was distilled via batch distillation such that all heavier components, including the $C_{14}$ MCHT and DMBP, were under 0.1 wt % in the overhead product of the distillation. This overhead product, comprising $C_7$ hydrocarbons and toluene (7.8 wt % MCH, 91.9 wt % toluene, ~0.3 wt % other species $C_{11}$ and smaller, ~0.1 wt % species over $C_{11}$), was dehydrogenated in the same parallel reactor unit, and over a dehydrogenation catalyst, as described in Example 3. The light stream and $H_2$ were fed at a 1:4 ratio at 2 WHSV into the reactor at 100 psig. As shown in FIG. 6, two different reaction temperatures were studied (400° C. and 450° C.). At 400° C., MCH conversion remained fairly stable, starting at around 80% and declining only slightly to about 70% after 300 hours on stream. At 450° C., MCH conversion remained steady at nearly 100% over the entire 400 hours on stream. Thus, even with toluene present, significantly higher conversion rates of MCH may be achieved by dehydrogenating MCH separately from heavier hydrocarbons.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" to require the listed components without excluding the presence of any other additional components. Likewise whenever a composition, an element or a group of elements is preceded with the transitional phrase "comprising", it is understood that we also contemplate the same composition or group of elements further narrowed with more restrictive transitional phrases such as "consisting essentially of," "consisting of", "selected from the group of consisting of," or "is" preceding the recitation of the composition, element, or elements and vice versa.

What is claimed is:

1. A process for producing biphenyl compounds, the process comprising:
   (a) contacting a hydroalkylation feed comprising $C_n$ aromatic hydrocarbons with hydrogen in the presence of a hydroalkylation catalyst under conditions effective to produce a hydroalkylation reaction effluent comprising (i) $C_{2n}$ cycloalkylaromatic compounds and (ii) $C_n$ saturated cyclic hydrocarbons, wherein n is an integer from 6 to 12;
   (b) providing at least a portion of the hydroalkylation reaction effluent to a first dehydrogenation zone, therein dehydrogenating at least a portion of the $C_{2n}$ cycloalkylaromatic compounds and at least a portion of the $C_n$ saturated cyclic hydrocarbons in the presence of a first dehydrogenation catalyst under conditions effective to produce a first dehydrogenation reaction product comprising (i) a mixture of $C_{2n}$ biphenyl compounds; (ii) recovered $C_n$ aromatic hydrocarbons; and (iii) unreacted $C_n$ saturated cyclic hydrocarbons;
   (c) separating the first dehydrogenation reaction product into (i) a heavy dehydrogenation stream rich in the $C_{2n}$ biphenyl compounds, and (ii) a light dehydrogenation stream rich in the recovered $C_n$ aromatic hydrocarbons and the unreacted $C_n$ saturated cyclic hydrocarbons;
   (d) providing at least a portion of the light dehydrogenation stream to a second dehydrogenation zone separate from the first dehydrogenation zone; and
   (e) in the second dehydrogenation zone, dehydrogenating at least a portion of the unreacted $C_n$ saturated cyclic hydrocarbons in the presence of a second dehydrogenation catalyst under conditions effective to produce a second dehydrogenation reaction product comprising additional recovered $C_n$ aromatic hydrocarbons;
   wherein:
   in step (a),
   the $C_n$ aromatic hydrocarbons are selected from the group consisting of benzene, toluene, ethylbenzene, xylene, and diethylbenzene;
   the $C_{2n}$ cycloalkylaromatic compounds are selected from the group consisting of cyclohexylbenzene, (methylcyclohexyl)toluene, (ethylcyclohexyl) ethylbenzene, (dimethylcyclohexyl)xylene, and (diethylcyclohexyl) diethylbenzene; and
   the $C_n$ saturated cyclic hydrocarbons are selected from the group consisting of cyclohexane, methylcyclohexane, dimethylcyclohexane, ethylcyclohexane, and diethylcyclohexane;
   in step (b),
   the $C_{2n}$ biphenyl compounds are each selected from the group consisting of biphenyl, dimethylbiphenyl, diethylbiphenyl, tetramethylbiphenyl, and tetraethylbiphenyl;
   the recovered $C_n$ aromatic hydrocarbons comprise the same compound or compounds as the $C_n$ aromatic hydrocarbons; and
   the unreacted $C_n$ saturated cyclic hydrocarbons comprise the same compound or compounds as the $C_n$ saturated cyclic hydrocarbons; and
   in step (e),
   the additional recovered $C_n$ aromatic hydrocarbons comprise the same compound or compounds as the $C_n$ aromatic hydrocarbons; and
   wherein the dehydrogenating (e) takes place in the presence of less than about 5.0 wt % $C_{2n}$ or higher hydrocarbons.

2. The process of claim 1, further comprising
   (f) recycling at least a portion of the second dehydrogenation reaction product such that it forms at least a part of the hydroalkylation feed for the hydroalkylation step (a).

3. The process of claim 2, wherein recycling at least a portion of the second dehydrogenation reaction product comprises
   (f-1) purifying the second dehydrogenation reaction product to obtain a purified second dehydrogenation reaction product; and
   (f-2) providing at least a portion of the purified second dehydrogenation reaction product as at least part of the hydroalkylation feed for the hydroalkylation step (a).

4. The process of claim 1, wherein:
   in step (a), the $C_n$ aromatic hydrocarbons are toluene, the $C_{2n}$ cycloalkylaromatic compounds are (methylcyclohexyl)toluene, and the $C_n$ saturated cyclic hydrocarbons are methylcyclohexane;
   in step (b), the $C_{2n}$ biphenyl compounds are dimethylbiphenyl, the recovered $C_n$ aromatic hydrocarbons are toluene, and the unreacted $C_n$ saturated cyclic hydrocarbons are methylcyclohexane; and
   in step (e), the additional recovered $C_n$ aromatic hydrocarbons are toluene.

5. The process of claim 1, further comprising:
   (g) contacting at least a portion of the heavy dehydrogenation stream obtained in step (c) with an oxidant under conditions effective to convert at least part of the $C_{2n}$ biphenyl compounds to biphenyl carboxylic acids; and (h) reacting the biphenyl carboxylic acids with one or more $C_1$-$C_{14}$ alcohols under conditions effective to produce biphenyl esters.

6. The process of claim 1, wherein n is an integer from 7 to 11, and further wherein:
   (I) the hydroalkylation feed in step (a) further comprises one or more $C_{n+1}$-$C_{12}$ aromatic hydrocarbons;
   (II) the hydroalkylation reaction effluent in step (a) further comprises (iii) one or more $C_{2n+2}$-$C_{24}$ cycloalkylaromatic compounds and (iv) one or more $C_{n+1}$-$C_{12}$ saturated cyclic hydrocarbons;
   (III) at least a portion of the one or more $C_{2n+2}$-$C_{24}$ cycloalkylaromatic compounds and at least a portion of the one or more $C_{n+1}$-$C_{12}$ saturated cyclic hydrocarbons are dehydrogenated in the first dehydrogenation zone in step (b) along with the portion of the $C_{2n}$ cycloalkylaromatic compounds and the portion of the $C_n$ saturated cyclic hydrocarbons, such that the first dehydrogenation reaction product in step (b) further comprises (iv) a mixture of $C_{2n+2}$-$C_{24}$ biphenyl compounds; (v) one or more recovered $C_{n+1}$-$C_{12}$ aromatic hydrocarbons; and (vi) unreacted $C_{n+1}$-$C_{12}$ saturated cyclic hydrocarbons; and
   (IV) the light dehydrogenation stream in step (c) further comprises at least a portion of the one or more recovered $C_{n+1}$-$C_{12}$ aromatic hydrocarbons and at least a portion of the unreacted $C_{n+1}$-$C_{12}$ saturated cyclic hydrocarbons.

7. The process of claim 1, wherein n is an integer from 6 to 10, and further wherein:
   (I) the hydroalkylation feed in step (a) further comprises one or more $C_{n+1}$-$C_{11}$ aromatic hydrocarbons;
   (II) the hydroalkylation reaction effluent in step (a) further comprises (iii) one or more $C_{2n+2}$-$C_{22}$ cycloalkylaromatic compounds and (iv) one or more $C_{n+1}$-$C_{11}$ saturated cyclic hydrocarbons;
   (III) at least a portion of the one or more $C_{2n+2}$-$C_{22}$ cycloalkylaromatic compounds and at least a portion of the one or more $C_{n+1}$-$C_{11}$ saturated cyclic hydrocarbons are dehydrogenated in the first dehydrogenation zone in step (b) along with the portion of the $C_{2n}$ cycloalkylaromatic compounds and the portion of the $C_n$ saturated cyclic hydrocarbons, such that the first dehydrogenation reaction product in step (b) further comprises (iv) a mixture of $C_{2n+2}$-$C_{22}$ biphenyl compounds; (v) one or more recovered $C_{n+1}$-$C_{11}$ aromatic hydrocarbons; and (vi) unreacted $C_{n+1}$-$C_{11}$ saturated cyclic hydrocarbons; and
   (IV) the light dehydrogenation stream in step (c) further comprises at least a portion of the one or more recovered $C_{n+1}$-$C_{11}$ aromatic hydrocarbons and at least a portion of the unreacted $C_{n+1}$-$C_{11}$ saturated cyclic hydrocarbons.

8. The process claim 1, wherein the at least a portion of the light dehydrogenation stream provided to the second dehydrogenation zone in step (d) comprises less than 1.0 wt % $C_{2n}$ or higher hydrocarbons.

9. The process of claim 1, wherein the rate of conversion of the unreacted $C_n$ saturated cyclic hydrocarbons to the additional recovered $C_n$ aromatic hydrocarbons in step (e) is at least about 90%.

10. The process of claim 1, wherein either or both of the first and second dehydrogenation catalysts of steps (b) and (e), respectively, comprises an element or compound thereof selected from group 10 of the Periodic Table of Elements.

11. The process of claim 1, wherein the dehydrogenating (e) takes place in the presence of less than 1.0 wt % $C_{2n}$ or higher hydrocarbons.

12. A process for producing biphenyl compounds, the process comprising:
   (a) contacting a hydroalkylation feed comprising at least one $C_n$ aromatic hydrocarbon with hydrogen in the presence of a hydroalkylation catalyst under conditions effective to produce a hydroalkylation reaction effluent comprising (i) a $C_{2n}$ cycloalkylaromatic compound and (ii) a $C_n$ saturated cyclic hydrocarbon, wherein n is an integer from 6 to 12;
   (b) separating the hydroalkylation reaction effluent into (i) a heavy hydroalkylation effluent rich in the $C_{2n}$ cycloalkylaromatic compound and (ii) a light hydroalkylation effluent rich in the $C_n$ saturated cyclic hydrocarbon;
   (c) providing at least a portion of the heavy hydroalkylation effluent to a first dehydrogenation zone and therein dehydrogenating at least a portion of the $C_{2n}$ cycloalkylaromatic compound in the presence of a first dehydrogenation catalyst under conditions effective to produce a heavy dehydrogenation reaction product comprising a mixture of $C_{2n}$ biphenyl compounds; and
   (d) providing at least a portion of the light hydroalkylation effluent to a second dehydrogenation zone separate from the first dehydrogenation zone, and therein dehydrogenating at least a portion of the $C_n$ saturated cyclic hydrocarbon in the presence of a second dehydrogenation catalyst under conditions effective to produce a light dehydrogenation reaction product comprising recovered $C_n$ aromatic hydrocarbon;
   wherein:
   in step (a),
   the $C_n$ aromatic hydrocarbon is selected from the group consisting of benzene, toluene, ethylbenzene, xylene, and diethylbenzene;
   the $C_{2n}$ cycloalkylaromatic compound is selected from the group consisting of cyclohexylbenzene, (methylcyclohexyl)toluene, (ethylcyclohexyl) ethylbenzene, (dimethylcyclohexyl)xylene, (diethylcyclohexyl)diethylbenzene and mixtures thereof; and
   the $C_n$ saturated cyclic hydrocarbon is selected from the group consisting of cyclohexane, methylcyclohexane, dimethylcyclohexane, ethylcyclohexane, diethylcyclohexane, and mixtures thereof;
   in step (c),
   the $C_{2n}$ biphenyl compounds are each selected from the group consisting of biphenyl, dimethylbiphenyl, diethylbiphenyl, tetramethylbiphenyl, tetraethylbiphenyl, and mixtures thereof; and
   in step (d),
   the recovered $C_n$ aromatic hydrocarbon comprises the same compound or compounds as the $C_n$ aromatic hydrocarbon; and
   wherein the at least a portion of the Cn saturated cyclic hydrocarbon is dehydrogenated in the presence of less than about 5.0 wt % $C_{2n}$ or higher hydrocarbons.

13. The process of claim 12, further comprising:
   (e) recycling at least a portion of the light dehydrogenation reaction product of step (d) such that it forms at least a part of the hydroalkylation feed in step (a).

14. The process of claim 13, wherein recycling at least a portion of the light dehydrogenation reaction product comprises:

(e-1) purifying the light dehydrogenation reaction product to obtain a purified light dehydrogenation reaction product; and (e-2) providing at least a portion of the purified light dehydrogenation reaction product as at least part of the hydroalkylation feed in step (a).

15. The process of claim 13, wherein:

in step (a), the $C_n$ aromatic hydrocarbon is toluene; the $C_{2n}$ cycloalkylaromatic compound is (methylcyclohexyl)toluene; and the $C_n$ saturated cyclic hydrocarbon is methylcyclohexane;

in step (c), the $C_{2n}$ biphenyl compounds are dimethylbiphenyl; and in step (d), the recovered $C_n$ aromatic hydrocarbon is toluene.

16. The process of claim 13, further comprising:

(f) contacting at least a portion of the heavy dehydrogenation reaction product of step (c) with an oxidant under conditions effective to convert at least part of the $C_{2n}$ biphenyl compounds to biphenyl carboxylic acids; and (g) reacting the biphenyl carboxylic acids with one or more $C_1$ to $C_{14}$ alcohols under conditions effective to produce biphenyl esters.

17. The process of claim 12, wherein n is an integer from 7 to 11, and further wherein:

(I) the hydroalkylation feed in step (a) further comprises one or more $C_{2n+1}$-$C_{12}$ aromatic hydrocarbons;

(II) the hydroalkylation reaction effluent in step (a) further comprises (iii) one or more $C_{2n+2}$-$C_{24}$ cycloalkylaromatic compounds and (iv) one or more $C_{n+1}$-$C_{12}$ saturated cyclic hydrocarbons;

(III) the light hydroalkylation effluent in step (b) further comprises at least a portion of the one or more $C_{n+1}$-$C_{12}$ saturated cyclic hydrocarbons; and (IV) at least a portion of the one or more $C_{n+1}$-$C_{12}$ saturated cyclic hydrocarbons are dehydrogenated in the second dehydrogenation zone in step (d) along with said at least a portion of the $C_n$ saturated cyclic hydrocarbon.

18. The process of claim 12, wherein n is an integer from 6 to 10, and further wherein:

(I) the hydroalkylation feed in step (a) further comprises one or more $C_{n+1}$-$C_{11}$ aromatic hydrocarbons;

(II) the hydroalkylation reaction effluent in step (a) further comprises (iii) one or more $C_{2n+2}$-$C_{22}$ cycloalkylaromatic compounds and (iv) one or more $C_{n+1}$-$C_{11}$ saturated cyclic hydrocarbons;

(III) the light hydroalkylation effluent in step (b) further comprises at least a portion of the one or more $C_{n+1}$-$C_{11}$ saturated cyclic hydrocarbons; and (IV) at least a portion of the one or more $C_{n+1}$-$C_{11}$ saturated cyclic hydrocarbons are dehydrogenated in the second dehydrogenation zone in step (d) along with said at least a portion of the $C_n$ saturated cyclic hydrocarbon.

19. The process of claim 12, wherein the light hydroalkylation effluent in step (b) comprises less than 0.1 wt % $C_{2n}$ or greater hydrocarbons.

20. The process of claim 12, wherein the rate of conversion of the $C_n$ saturated cyclic hydrocarbon to recovered $C_n$ aromatic hydrocarbon in step (d) is at least about 90%.

21. The process of claim 12, wherein either or both of the first and second dehydrogenation catalysts of steps (c) and (d), respectively, comprises an element or compound thereof selected from group 10 of the Periodic Table of Elements.

22. The process of claim 12, wherein the at least a portion of the $C_n$ saturated cyclic hydrocarbon is dehydrogenated in the presence of less than 1.0 wt % $C_{2n}$ or higher hydrocarbons.

* * * * *